United States Patent [19]

Anderson et al.

[11] Patent Number: 5,591,720
[45] Date of Patent: Jan. 7, 1997

[54] OLIGONUCLEOTIDES FOR MODULATING THE EFFECTS OF CYTOMEGALOVIRUS INFECTIONS

[75] Inventors: Kevin P. Anderson, Carlsbad, Calif.; Kenneth G. Draper, Richmond, Ohio

[73] Assignee: Isis Pharmaceuticals, Inc., Carlsbad, Calif.

[21] Appl. No.: 927,506

[22] PCT Filed: Aug. 14, 1991

[86] PCT No.: PCT/US91/05815

§ 371 Date: Nov. 19, 1992

§ 102(e) Date: Nov. 19, 1992

Related U.S. Application Data

[63] Continuation-in-part of Ser. No. 568,366, Aug. 16, 1990, abandoned.

[51] Int. Cl.⁶ .......................... A61K 31/70; G07H 21/04
[52] U.S. Cl. .................................. 514/44; 536/24.5
[58] Field of Search ............................ 536/24.5; 514/44

[56] References Cited

PUBLICATIONS

Stein et al., Science 261:1004–1012 (20 Aug. 1993).
Cranage et al., Identification and expression of a human CMV glycoprotein with homology to the EBV BXLF2 product . . . , J. Virology 62(4):1416–1422 (Apr. '88).
Kouzarides et al., Sequence and transcription analysis of the human CMV DNA polymerase gene, J. Virology 61(1):125–133 (Jan. '87).
Ratner, Can the antisense message be delivered?, Biotechnology 7:207 (Mar. '89).
Spacte et al., Human CMV strain Towne glycoprotein B is processed by proteolytic cleavage, Virology 167:207–225 (1988).
Stenberg et al., Structural analysis of the major immediate early gene of human CMV, J. Virology 49(1):190–199 (Jan. '84).
Stenberg et al., Multiple spliced and unspliced transcripts from human CMV immediate–early region 2 . . . , J. Virology 56(3):665–675 (Dec. '85).
Zon, Oligonucleotide analogues as potential chemotherapeutic agents, Pharm. Res. 5(9):539–549.
Cohen in Oligonucleotides: Antisense Inhibitors of Gene Expression, CRC Press, Boca Raton, Florida 1989.
P. S. Miller et al., A new approach to chemotherapy based on molecular biology and nucleic acid chemistry: Matagen (masking tape for gene expression), Anti–Cancer Drug Design, vol. 2, pp. 117–129 1987.
Rothenberg, et al., Oligodoexynucleotides as Anti–Sense Inhibitors of Gene Express: Therapeutic Implications, J. Natl. Cancer Inst., 81:1539–1544 1989.

Primary Examiner—Stephanie W. Zitomer
Attorney, Agent, or Firm—Law Offices of Jane Massey Licata

[57] ABSTRACT

Compositions and methods for modulating the effects of cytomegalovirus (CMV) infections are disclosed, comprising contacting CMV mRNA with an oligonucleotide or oligonucleotide analog which can bind with at least portions of the CMV RNA. In accordance with the preferred embodiments, oligonucleotides or oligonucleotide analogs are designed to bind with portions of the CMV mRNAs which code for the IE1, IE2 or DNA polymerase proteins. In accordance with a preferred embodiment, methods of treatment of human cytomegalovirus are disclosed.

2 Claims, 4 Drawing Sheets

OLIGONUCLEOTIDES FOR MODULATING THE EFFECTS OF CYTOMEGALOVIRUS INFECTIONS

This is a continuation-in-part application of application Ser. No. 568,366, filed Aug. 16, 1990, now abandoned.

FIELD OF THE INVENTION

This invention relates to the design and synthesis of antisense oligonucleotides which can be administered to inhibit the replication of cytomegalovirus and treat cytomegalovirus infections. These compounds can be used either prophylactically or therapeutically to reduce the severity of disease caused by cytomegaloviruses. Oligonucleotides and oligonucleotide analogs which are specifically hybridizable with RNA targets are described.

BACKGROUND OF THE INVENTION

Cytomegaloviruses (CMV's) are ubiquitous in nature and are the most common causes of intrauterine infection. Congenital infection is common in newborns of infected mothers. In some populations, as much as 10% of children display perinatal infections. In a small percentage of newborns, the infection is virulent, involving multiple organs. Pronounced involvement of the reticuloendothelial and central nervous system is typical; and the infection is a major cause of mental retardation. Careful testing demonstrates that as many as 50% of severely, prenatally infected adults may display neuropsychiatric disease or deafness. Although extraneural organs are usually spared chronic morbidity, the virus can be detected in the kidney for years.

In the adult, cytomegalovirus-induced mononucleosis is a lingering illness that causes significant morbidity. If it occurs in immunosuppressed patients, the disease is more severe, and it may be complicated by other infectious pathogens which may be fatal. Cytomegalovirus retinitis is a severe problem in immunosuppressed patients that often leads to blindness. Immunosuppressed patients are also very susceptible to CMV pneumonitis, which is one of the most lethal of human viral diseases. Although cytomegalovirus may play a role in the progression of HIV infection to AIDS by stimulating the transcription of the HIV long terminal repeats (LTR) in non-transformed co-infected T cells, histologic examination of adrenals and brains from AIDS patients has suggested that the adrenalitis, encephalitis and peripheral neuropathy were caused by CMV infection.

CMV is considered to be an oncogenic virus. In vitro, CMV can transform cells and stimulate growth. Both human and non-human cells can undergo transformation when incubated with CMV. Transformed cells contain CMV antigens that are oncogenic when inoculated into appropriate animals. Moreover, oncogenic potential has been associated with specific segments of the CMV genome.

Human CMV is a large, enveloped herpesvirus whose genome consists of a double-stranded DNA molecule which is approximately 240,000 nucleotides in length. This genome is the most complex of all DNA viruses and is approximately 50% larger than the genome of herpes simplex virus (HSV). Intact viral DNA is composed of contiguous long (L) and short (S) segments, each of which contains regions of unique DNA sequence flanked by homologous regions of repetitive sequence. As a group, the human CMV isolates share at least 80% sequence homology, making it nearly impossible to classify cytomegaloviruses into subgroups or subtypes, although variations in the restriction endonuclease patterns of various CMV DNA preparations are identifiable in epidemiologically unrelated strains. The DNA of the prototypic strain of CMV (AD 169) has been sequenced and reported to contain a conservative estimate of 175 unique translational open reading frames (ORFs). A number of the predicted CMV gene products show homology to other human herpesvirus gene products. At least 42 ORFs encode putative glycoproteins and several of the CMV ORFs putatively encode proteins with amino acid homology to human opsin receptor proteins.

In permissive human fibroblasts, CMV gene expression is regulated by a cascade of genetic events that act at both the transcriptional and translational levels. CMV gene expression can be divided into three phases which resemble those of HSV defined as the immediate early (IE), early and late periods. Following adsorption, penetration and uncoating of the virus, a group of viral transcripts, immediate early messenger RNAs (IE mRNAs) are synthesized within 1–4 hours even in the presence of translational inhibitors such as cycloheximide. In the normal course of infection, the IE mRNAs are translated and their protein products are instrumental in the onset of early transcriptional events. At least 4 proteins are synthesized from IE mRNAs; of these, one is a glycoprotein. The IE1 and IE2 proteins are transcriptional activating factors for other CMV genes and the IE3 protein encompasses a region of the CMV genome which can transform NIH 3T3 cells in vitro. Early proteins are encoded by the mRNAs which are synthesized prior to viral DNA synthesis. A number of the early proteins play a role in nucleotide metabolism and DNA synthesis in the infected cell. After the onset of viral DNA synthesis, the transcription of the late mRNAs is maximal and probably reflects a template abundancy requirement similar to that observed for analogous HSV mRNAs. The late CMV proteins include the glycoprotein constituents of the viral envelope, the viral capsid proteins and other proteins which are necessary for assembly or structural integrity of the mature CMV particle and/or egress of the assembled virion from the infected cell. In addition to the transcriptional controls operant upon CMV gene expression, examples of post-transcriptional controls are known to influence the appearance of some CMV proteins. Splicing of mRNAs is more common than observed in HSV gene expression and the nucleotide sequence composition of the 5' nontranslated region in the cognate mRNA is reported to influence the synthesis of at least one early CMV protein.

Effective therapy for CMV has not yet been developed despite studies on a number of antivirals. Interferon, transfer factor, adenine arabinoside (Ara-A), acycloguanosine (Acyclovir, ACV) and certain combinations of these drugs have been ineffective in controlling CMV infection. Based on preclinical and clinical data, foscarnet (PFA) and ganciclovir (DHPG) show limited potential as antiviral agents. PFA treatment has resulted in the resolution of CMV retinitis in five AIDS patients. DHPG studies have shown efficacy against CMV retinitis or colitis. DHPG seems to be well tolerated by treated individuals, but the appearance of a reversible neutropenia, the emergence of resistant strains of CMV upon long-term administration, and the lack of efficacy against CMV pneumonitis limit the long term applications of this compound. The development of more effective and less-toxic therapeutic compounds and methods is needed for both acute and chronic use.

Classical therapeutics has generally focused upon interactions with proteins in efforts to moderate their disease causing or disease potentiating functions. Such therapeutic approaches have failed for cytomegalovirus infections. The present invention is directed to an alternative approach to the treatment of such infections, the antisense inhibition of cytomegalovirus gene expression through the mediation of oligonucleotides or oligonucleotide analogs.

Antisense methodology is the complementary hybridization of relatively short oligonucleotides to single-stranded mRNA or single-stranded DNA, or even double stranded DNA, such that the normal, essential functions of these intracellular nucleic acids are disrupted. Hybridization is the sequence specific hydrogen bonding of oligonucleotides to Watson-Crick base pairs of RNA or single stranded DNA. Such base pairs are said to be complementary to one another.

The events which disrupt nucleic acid function are discussed by Cohen in Oligonucleotides: Antisense Inhibitors of Gene Expression, CRC Press, Boca Raton Fla., (1989) who proposes two possible types of terminating events. The first, hybridization arrest, denotes a terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides; P. S. Miller & P.O.P. Ts'O, *Anti-Cancer Drug Design*, Vol. 2, pp. 117–128 (1987); and α-anomer oligonucleotides, Cohen J. S. ed., *Oligonucleotides: Antisense Inhibitors of Gene Expression*, CRC Press, Boca Raton Fla. (1989) are two of the most extensively studied antisense agents which are thought to disrupt nucleic acid function by hybridization arrest.

A second type of terminating event for antisense oligonucleotides involves enzymatic cleavage of the targeted RNA by intracellular RNase H. The oligonucleotide or oligonucleotide analog, which must be of the deoxyribo type, hybridizes with the targeted RNA and this duplex activates the RNase H enzyme to cleave the RNA strand, thus destroying the normal function of the RNA. Phosphorothioate oligonucleotides are a prominent example of an antisense agent which operates by this type of terminating event.

Considerable research is being directed to the application of oligonucleotides and oligonucleotide analogs as antisense agents for therapeutic purposes. Applications of oligonucleotides as diagnostics, research reagents, and potential therapeutic agents require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides towards nuclease degradation.

Oligonucleotides and analogs modified to exhibit resistance to nucleases, to activate the RNase H terminating event, and to hybridize with appropriate strength and fidelity to targeted RNA (or DNA) are greatly desired for antisense oligonucleotide diagnostics, therapeutics and research with cytomegaloviruses.

OBJECTS OF THE INVENTION

It is an object of this invention to provide oligonucleotides and oligonucleotide analogs which are capable of hybridizing with messenger RNA of cytomegalovirus to inhibit the function of the messenger RNA.

It is a further object to provide oligonucleotides and analogs which can modulate the expression of cytomegalovirus through antisense interaction with messenger RNA of the virus.

Yet another object of this invention is to provide methods of diagnostics and therapeutics for cytomegalovirus in animals.

Methods, materials and kits for detecting the presence or absence of cytomegalovirus in a sample suspected of containing it are further objects of the invention.

Novel oligonucleotides and oligonucleotide analogs are other objects of the invention.

These and other objects will become apparent to persons of ordinary skill in the art from a review of the instant specification and appended claims.

SUMMARY OF THE INVENTION

In accordance with the present invention, methods of modulating the effects of cytomegalovirus infection are provided. Oligonucleotides and oligonucleotide analogs having a sequence of nucleotide bases specifically hybridizable with a selected sequence of a cytomegalovirus RNA are provided. It has been determined that targeting cytomegalovirus mRNA coding for the IE1, IE2, or DNA polymerase proteins is a key to the effective antisense therapy with these oligonucleotides or oligonucleotide analogs. Methods for treating disease states by administering oligonucleotides or oligonucleotide analogs, either alone or in combination with a pharmaceutically acceptable carrier, to animals suspected of having cytomegalovirus infections are provided.

This relationship is commonly denoted as "antisense." The oligonucleotides and oligonucleotide analogs are able to inhibit the function of RNA—either its translation into protein, its translocation into the cytoplasm, or any other activity necessary to its overall biological function. The failure of the RNA to perform all or part of its function results in failure of a portion of the genome controlling the normal life cycle of the virus.

It has now been found that oligonucleotides or oligonucleotide analogs can be designed especially for cytomegalovirus infections which are effective in diminishing the infection. It is preferred that oligonucleotides and analogs have between about 5 and about 50 nucleic acid base units. It is preferred that the oligonucleotide or analog be specifically hybridizable with mRNA coding for the CMV IE1, IE2, or DNA polymerase proteins. The oligonucleotide analog may be modified to reduce nuclease resistance and to increase their efficacy.

In accordance with preferred embodiments, the mRNA is interfered with to an extent sufficient to inhibit CMV replication. Thus, oligonucleotides and oligonucleotide analogs which are capable of interacting with portions of CMV mRNA are comprehended. Animals suspected of having the disease are contacted with an oligonucleotide or oligonucleotide analog made in accordance with this invention. In particular, the present invention is believed to be effective in the treatment of cytomegalovirus infections, either prophylactically or therapeutically.

DETAILED DESCRIPTION OF PREFERRED EMBODIMENTS

Figure 1:
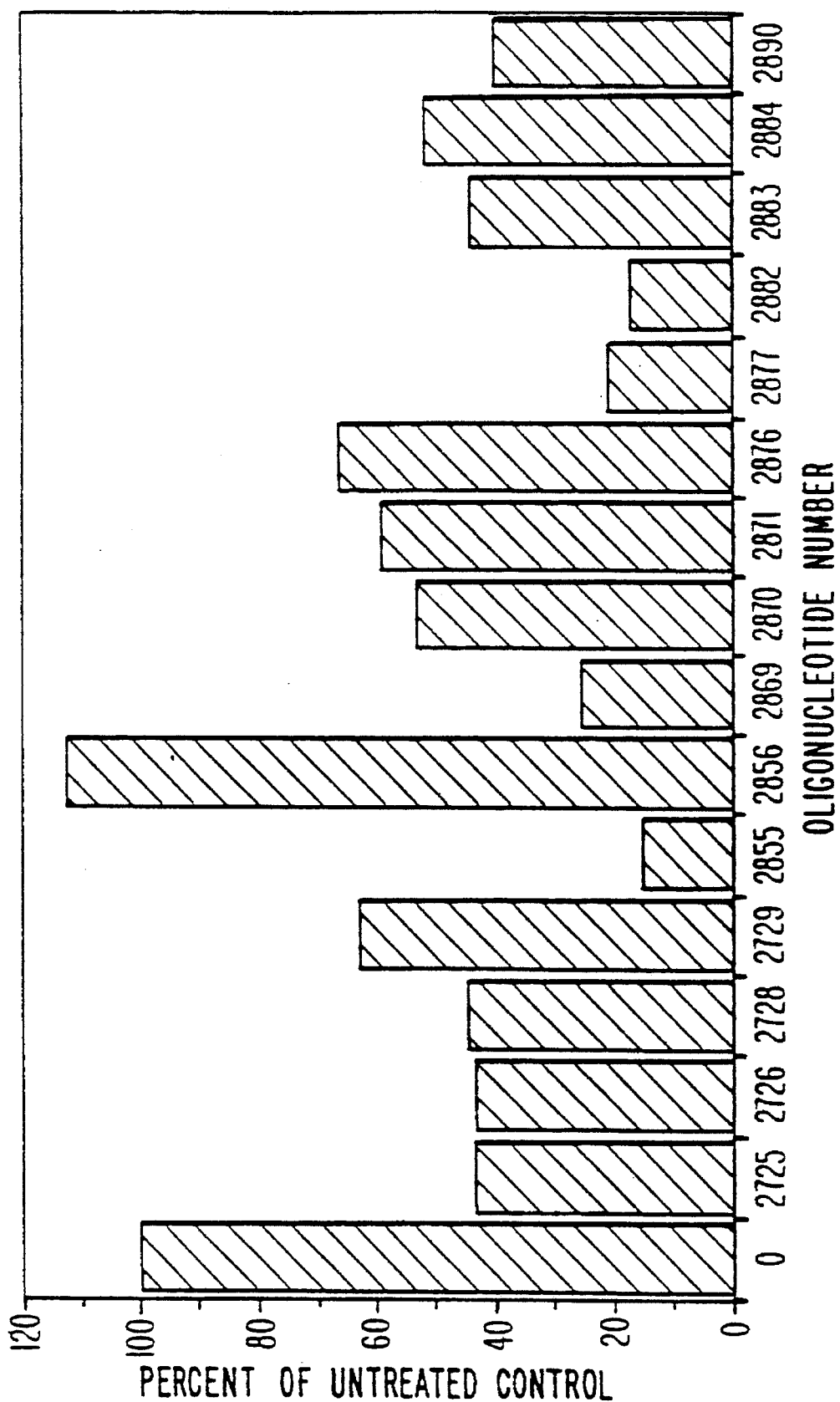
FIG. 1 is a bar graph showing the antiviral activity of oligonucleotides 2725 through 2890 against cytomegalovirus.

Antisense oligonucleotides hold great promise as therapeutic agents for the treatment of many human diseases. Oligonucleotides specifically bind to the complementary sequence of either pre-mRNA or mature mRNA, as defined by Watson-Crick base pairing, inhibiting the flow of genetic information from DNA to protein. Numerous recent studies have documented the utility of antisense oligonucleotides as biochemical tools for studying target proteins. Rothenberg et. al., *J. Natl. Cancer Inst.* 81:1539–1544 (1989); Zon, G. *Pharmaceutical Res.*, 5:539–549 1987). Because of recent advances in oligonucleotide chemistry, synthesis of nuclease-resistant oligonucleotides, and availability of types of oligonucleotide analogs which exhibit enhanced cell uptake, it is now possible to consider the use of antisense oligonucleotides as a novel form of therapeutics.

For therapeutics, an animal suspected of having a cytomegalovirus infection is treated by administering oligonucleotides or oligonucleotide analogs in accordance with this invention. Persons of ordinary skill can easily determine optimum dosages, dosing methodologies and repetition rates. Such treatment is generally continued until either a cure is effected or a diminution in the disease state is achieved.

It is to be expected that differences in the DNA of cytomegalovirus from different species and from different types within a species exist. Thus, it is believed, for example, that the regions of the various cytomegalovirus species serve essentially the same function for the respective species and that interference with expression of the genetic information will afford similar results in the various species. This is believed to be so even though differences in the nucleotide sequences among the species doubtless exist.

Accordingly, nucleotide sequences set forth in the present specification will be understood to be representational for the particular species being described. Homologous or analogous sequences for different species of cytomegalovirus are specifically contemplated as being within the scope of this invention.

The present invention employs oligonucleotides and oligonucleotide analogs for use in antisense inhibition of the function of cytomegalovirus RNA. In the context of this invention, the term "oligonucleotide" refers to a polynucleotide formed from naturally occurring bases and pentofuranosyl groups joined by native phosphodiester bonds. This term effectively refers to naturally-occurring species or synthetic species formed from naturally-occurring subunits or their close homologs.

"Oligonucleotide analog," as that term is used in connection with this invention, refers to moieties which function similarly to oligonucleotides but which have non-naturally occurring portions. Thus, oligonucleotide analogs may have altered sugar moieties or inter-sugar linkages. Exemplary among these are the phosphorothioate and other sulfur-containing species which are known for use in the art. In accordance with some preferred embodiments, least some of the phosphodiester bonds of the oligonucleotide have been substituted with a structure which functions to enhance the ability of the compositions to penetrate into the region of cells where the RNA or DNA whose activity to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotide analogs may also include species which include at least some modified base forms. Thus, purines and pyrimidines other than those normally found in nature may be so employed. Similarly, modifications on the pentofuranosyl portions of the nucleotide subunits may also occur as long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention so long as they function effectively to hybridize with cytomegalovirus RNA. The oligonucleotides and oligonucleotide analogs in accordance with this invention preferably comprise from about 3 to about 50 nucleic acid base units. It is more preferred that such oligonucleotides and analogs comprise from about 8 to 25 nucleic acid base units, and still more preferred to have from about 12 to 25 nucleic acid base units. As will be appreciated, a nucleic acid base unit is a base-sugar combination suitably bound to adjacent nucleic acid base unit through phosphodiester or other bonds.

The oligonucleotides and analogs used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotide analogs such as the phosphorothioates and alkylated derivatives.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, and intron/exon junction ribonucleotides. Thus, oligonucleotides and oligonucleotide analogs may be formulated in accordance with this invention which are targeted wholly or in part to these associated ribonucleotides as well as to the informational ribonucleotides. In preferred embodiments, the oligonucleotide or analog is specifically hybridizable with a transcription initiation site, a translation initiation site, an intron/exon junction or sequences in the 5'- or 3'-untranslated region.

The HCMV genome is the most complex of the herpes viruses in terms of its genomic structure. Replication-defective mutants of HCMV have only been isolated for two viral genes, the immediate early complex (IE1 or IE2) and the DNA polymerase. These genes are known to play major roles in HCMV gene expression. They have been selected as primary targets for antisense compound design. Secondary target genes for the design of therapeutic antisense oligonucleotides and analogs have been selected by analogy to genes of herpes simplex virus. Such genes have been determined to be essential for herpes simplex virus replication and/or sensitive to antisense inhibition. Four gene products of herpes simplex virus which have recently shown to be sensitive to antisense inhibition are the virion tegument protein (UL48), the two proteins constituting the ribonucleotide reductase enzyme (UL39,40) and a virion phosphotransferase (UL13). Other herpes simplex virus genes which are currently being studied are the auxiliary DNA replication enzymes (UL5, 8, 9, 29, 42, 52) and the major capsid protein (UL36). HCMV encodes proteins which have been identified as potentially analogous in function to each of these herpes simplex virus proteins; these genes have been selected to serve as secondary targets in connection with this invention.

The molecular biology of immediate early transcription in HCMV has been as well elucidated as that of any transcriptional unit in the eucaryotic cell. Briefly, synthesis of the major immediate early transcript (IE1) is controlled by a number of repeat units 5' of the mRNA cap site. These repeats are responsive to a number of transcriptional response molecules known to operate in cell-specific and differentiation specific manners. The IE1 mRNA is an abundant RNA which is 1.9 kb in length and encodes a protein which migrates with an apparent molecular weight of 72 kDa on PAGE-SDS. This protein has been found in virions and controls the expression of itself as well as that of the IE2 gene product. At the initial phase of immediate early transcription, only IE1 mRNA is synthesized by the cellular RNA polymerase. A small amount of IE2 mRNA is made by processing of the IE1 mRNA during this early time of infection. Over time, levels of IE1 protein accumulate and bind the promoter region of the IE1 gene, repressing further transcription of the IE1 mRNA and allowing a weaker downstream promoter for the IE2 gene to control further synthesis of IE2 mRNA. It has been proposed that the IE1 gene product may serve to boost viral transcription during a productive infection and alternatively to activate viral gene expression from the latent state. The observation of cell-type and differentiation or hormonal responsive elements in the promoter of the IE1 gene are consistent with this proposition. The IE2 protein is capable of transcriptionally activating many of the HCMV early and late genes in a manner similar to other known transactivating proteins of cellular and vital Origin. Thus, the IE2 protein is believed to be one of the master switches for HCMV gene expression. The other controlling switch of CMV genes is the DNA polymerase protein. Transcription of the late viral genes operates at very low levels until the onset of viral DNA replication, after which the late genes are activated by an increased template availability. The exact molecular condition which is operant in this enhanced template availability is unclear, but the presence of the viral DNA polymerase and replication of the genome are essential requirements for the observed effect.

The selected targets within the mRNA sequences include regions of the mRNA which are known to control mRNA stability, processing and/or translational efficiency. These target sites include the 5' cap regions and translation initiation control regions. The target sequences for the IE1, IE2, and DNA polymerase genes are set forth in Table 1:

TABLE 1

TARGET SEQUENCES FOR CYTOMEGALOVIRUS
Oligonucleotide SYNTHESIS

| TARGET GENE | TARGET REGION | TARGET DNA SEQUENCE |
|---|---|---|
| DNA POLYMERASE | mRNA CAP SITE | GGACCGGGACCACCGTCGTC |
| DNA POLYMERASE | AUG REGION | GTCCGCTATGTTTTTCAACCC |
| DNA POLYMERASE | CONSERVED AA (717–732) | CCTTCCATCATCATGGCCCAC |
| DNA POLYMERASE | CONSERVED AA (905–914) | GGCGCGGGTCATCTACGGGAC |
| DNA POLYMERASE | CMV INSERTION (608–697) | CCGCTGTGCCCGGCGACGCGG CCGCCCTTGCAATCTGCGCCG GGCGTTTCACCCGGCTCCGGC |
| DNA POLYMERASE | (1109–1159) | GCGCCCGGTGTCCGGACGGCG CCGCCGGCGTGGTTTCCCGGT CCGGCAAAGAAGAGGGCGCGG |
| IE1 | mRNA CAP SITE | GTGAACCGTCAGATCGCCTGG |
| IE1 | AUG REGION | CTTGACACGATGGAGTCCTC |
| IE1 | I/E-1 | GCCAAGAGTGACGTAAGTACC |
| IE1 | I/E-2 | GTCTTTTCTGCAGTCACCGTC |
| IE1 | I/E-3 | CAAGGTGCCACGGTACGTGTC |
| IE1 | I/E-4 | CATGTGTTTAGGCCCGAGAC |
| IE1 | I/E-5 | GGCAGAACTCGGTAAGTCTG |
| IE1 | I/E-6 | CCTCCTCTACAGTCAAACAG |
| IE2 | AUG/ CAP SITE | GCGCCTATCATGCTGCCCCTC |
| IE2 | AUG REGION | GCTCTCCCAGATGAACCACCC |
| IE2 | I/E-1 | CAAGATTGACGAGGTGAGCCG |
| IE2 | I/E-2 | CCCAAACAGGTCATGGTGCGC |
| IE2 | NUC SIG-1 | GCGTAAGAAACCGCGCAAAAC |
| IE2 | NUC SIG-2 | CGCAAGAAGAAGAGCAAACGC |

In Table 1, the abbreviation I/E refers to the intron/exon junction while the AUG region is the translation initiation region of IE2 mRNA whose transcription is controlled by the IE2 specific promoter region. The abbreviation "nuc sig" refers to nuclear localization signals of the IE2 protein.

Oligonucleotides or analogs useful in the invention are complementary to the DNA (especially for oligonucleotides directed to intron/exon junctions) or to the corresponding messenger RNA (mRNA) or pre-messenger RNA. Thus, the oligonucleotides and analogs in accordance with the invention preferably have one of the foregoing sequences or an effective portion thereof. Thus, it is preferred to employ any of these oligonucleotides (or their analogs) as set forth above or any of the similar nucleotides which persons of ordinary skill in the art can prepare from knowledge of the preferred antisense targets for the modulation of the viral infection.

The oligonucleotides and oligonucleotide analogs of this invention can be used in diagnostics, therapeutics and as research reagents and kits. For therapeutic use, the oligonucleotide or oligonucleotide analog is administered to an animal suffering from a cytomegalovirus infection. It is generally preferred to apply the therapeutic agent in accordance with this invention internally such as intravenously, transdermally or intramuscularly. Other forms of administration such as topically or intralesionally may also be useful. Inclusion in suppositories is presently believed to be likely to be useful. Use of the oligonucleotides and oligonucleotide analogs of this invention in prophylaxis is also likely to be useful. Such may be accomplished, for example, by providing the medicament as a coating in condoms and the like. Use of pharmacologically acceptable carriers is also preferred for some embodiments.

The present invention is also useful in diagnostics and in research. Since the oligonucleotides and oligonucleotide analogs of this invention hybridize to nucleic acid from cytomegalovirus, sandwich and other assays can easily be constructed to exploit this fact. Provision of means for detecting hybridization of oligonucleotide or analog with cytomegalovirus present in a sample suspected of containing it can routinely be accomplished. Such provision may include enzyme conjugation, radiolabelling or any other suitable detection systems. Kits for detecting the presence or absence of cytomegalovirus may also be prepared.

EXAMPLES

EXAMPLE 1

Cells and Virus:

Human foreskin fibroblast (ATCC #CRL 1635) cells used are obtained from the American Tissue Culture Collection. Cultures are grown in Dulbecco's Modified Eagle's Medium with 4.5 g/L glucose (high glucose DMEM) and supplemented with 10% fetal bovine serum (FBS), penicillin (100 units/ml), streptomycin (100 micrograms/ml) and L-glutamine (2 mM). Stock cultures of human cytomegalovirus (HCMV strain AD169 or Towne) are grown on foreskin cells using low multiplicity infections (multiplicity of infection [MOI]=0.02 plague forming units [PFU]/cell).

To assess the ability of oligonucleotides to inhibit CMV replication, an infectious yield assay will be used. To perform this assay, foreskin cells are seeded at a density of $5\times10^5$ cells per well in Falcon 6 well tissue culture plates. Cells are overlaid with 2 ml of medium (high glucose DMEM with 10% FBS) and incubated at 37° C. for 18–24 hours. Where appropriate, cells are overlaid with oligonucleotide preparations in 1 ml of medium at 24 hours after seeding the plates. Following an 18 hour incubation, all wells are rinsed with phosphate buffered saline and infected with HCMV at varying MOIs suspended in 0.5 ml of serum-free hgh glucose DMEM. Virus and cells are incubated at 37° C. for 90 minutes on a rocking platform. Following viral adsorption, unadsorbed virus is rinsed away by washing with phosphate buffered saline. Where appropriate, 1 ml of medium (high glucose DMEM with 10% FBS) containing 10 μM concentrations of oligonucleotide are added to the well and the cells are incubated for 4–5 days at 37° C. Control wells receive 1 ml of medium which contains no oligonucleotide.

Virus is harvested into the overlay medium and triplicate wells of each experimental point are combined. The suspension is frozen at −80° C. Virus titer is determined for each sample by plaque assay on human foreskin cell monolayers. Dilutions of each virus preparation are prepared and duplicate aliquots of each dilution are absorbed onto foreskin cells for 90 minutes with rocking. After adsorption, the unadsorbed virus inoculum is removed by rinsing the plates with phosphate buffered saline and the cells are overlaid with 2 ml of high glucose DMEM containing 5% FBS and 0.75% methyl cellulose. Cells are incubated at 37° C. for 12–14 days before plagues are fixed with formalin, stained with crystal violet and counted. Plague counts from treated wells are compared with those from the control wells to establish the degree of inhibition of infectious virus production.

It is anticipated that treatment of CMV-infected cells with 10 μM concentrations of phophorothioate oligonucleotides which exhibit sequence complementarity to the CMV IE1, IE2 or DNA polymerase mRNAs will reduce the infectious yield of virus by 90%.

EXAMPLE 2

The mechanism of action of active CMV antisense compounds can also be validated. The molecular nature of any mechanism of action study is dictated by the CMV gene sequence which is the target of oligonucleotide inhibition. The most direct assays take advantage of the biological function of the protein encoded by the target CMV gene. The biological activity of an enzymatic protein often amplifies the end signal of such an assay so that the assay is very sensitive to even small changes in vital protein levels. Examples of CMV genes which are amenable to these types of assays are the DNA polymerase and IE1 & 2 loci.

For the DNA polymerase protein, a simple mechanistic assay involves assessing the ability of target specific oligonucleotides to inhibit the incorporation of $^3$H-thymidine into vital DNA under conditions which favor viral DNA polymerass activity over cellular DNA polymerase activity. The ability of the CMV IE proteins to transactivate RNA synthesis of certain CMV genes has been used to devise a transient gene expression assay, whose activity depends upon the presence of biologically active IE1 or IE2 proteins in an infected cell. Briefly, IE1 or IE2 responsive promoter regions are cloned 5' of an indicator gens (e.g., bacterial chloramphenicol acetyl transferase, CAT) in a plasmid vector. The vector is introduced into human foreskin cells, which in turn are infected with HCMV. The detection of CAT activity can be determined from cell lysates and CAT activity levels used to indirectly quantitate IE1 or IE2 protein levels. The effect of oligonucleotides on the CAT activity will be compared for both the IE1 and IE2 responsive constructs.

In cases in which an overt biological activity is not easily demonstrable, oligonucleotide-induced changes in protein levels can be determined by immuneprecipitation of infected cell proteins, gel electrophoresis of the immuneprecipitate in an SDS-acrylamide matrix, and detection of target protein levels by autoradiography of the gel. Proteins of assayable biological activity can also be quantitated by immuneprecipitation and gel electrophoretic techniques.

EXAMPLE 3

The value of a CMV antisense drug will in a large degree depend on its ability to specifically interact with CMV RNA targets without adversely effecting host cell functions. Therefore it is important to evaluate the potential for non-specific interactions and toxicities of active compounds. The potential for these adverse reactions is accessed in numerous models of acute and chronic cellular toxicity. Initially, active compounds are evaluated for toxicity in infected human foreskin cells using $^3$H-leucine and $^3$H-thymidine to measure effects on protein and DNA synthesis, respectively. From determinations of the oligonucleotide LD50 in these assays and the ID50 activity values obtained in the primary and secondary activity screens, a therapeutic index (T.I.) for each active oligonucleotide compound is determined. Only those compounds exhibiting T.I. more than 100 are then considered for subsequent evaluation.

EXAMPLE 4

Synthesis and characterization of oligonucleotides and analogs:

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1, 2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Trisborate buffer, pH 7.0. Oligonucleotidedeoxynucleotides and their phosphorothioate analogs were judged from electrophoresis to be greater than 80% full length material.

EXAMPLE 5

ELISA assay for inhibition of HCMV replication by antisense olionucleotides:

Oligonucleotides complementary to human cytomegalovirus mRNA were tested for antiviral activity in an ELISA-based assay of HCMV replication. Normal human dermal fibroblasts (Clonetics Corp., San Diego Calif.) were grown in serum-free medium (Clonetics) and used to seed 96-well plates. When cells are approximately 80% confluent, they are pretreated with oligonucleotides. Approximately 20 hours after pretreatment the medium (containing oligonucleotides) is carefully poured off and the cells washed twice with warmed fibroblast basal medium (FBM, Clonetics). Cells are then infected with 100 µl/well of CMV stock diluted in FBM. The plates are incubated at 37° C. for two hours. The medium (containing virus) is then carefully poured off and replaced with fresh, prewarmed FBM medium, 100 µl per well. The plates are briefly incubated at 37° C. and then 5 µl of oligonucleotide, diluted in FBM, is reintroduced into the medium in each well. Two days later, cells are post-treated again with oligonucleotides in the same way. On day six, the plates are prepared for ELISA.

In preparation for ELISA, the medium is carefully poured off the plates, and cells are fixed in 200 µl of absolute ethanol per well. Cells are fixed for 30 minutes at room temperature, then ethanol is removed and plates are air-dried. Plates are blocked for one hour prior to ELISA with PBS containing 2% BSA. Blocking solution is removed and 100 µl of an anti-CMV antibody, diluted 1:2000 in PBS with 1% BSA, is added. Cells are incubated in antibody for one hour at 37° C. and washed three times in PBS. The secondary antibody, biotinylated goat anti-mouse IgG (Bethesda Research Labs, Md.), is diluted 1:1000 in PBS with 1% BSA, and incubated with cells for one hour at 37° C. Cells are then washed and incubated for one hour at 37° C. in streptavidin-B-D-galactosidase. Color is developed with chlorophenol red-B-D-galactopyranoside, 20 mg dissolved in 10 ml of 50 mM Na Phosphate, 1.5 mM MgCl2; plates are shaken for 10 minutes and the absorbance is read at 575 nm.

Twenty-four oligonucleotides complementary to HCMV were tested for antiviral activity. The sequences and gene targets for these oligonucleotides are presented in Table 2.

TABLE 2

Oligonucleotides Tested for Activity Against CMV

| SEQ ID NO | ISIS # | NUCLEOTIDE #s | TARGET | SEQUENCE | TYPE |
|---|---|---|---|---|---|
| 1  | 2725 |               | Nonsense      | GTG TCA AGT GGC ACC ATA CG  | P = S |
| 2  | 2726 |               | Nonsense      | TGG AAA GTG TAC ACA GGC GAA | P = S |
| 3  | 2728 | 80618–80638   | DNA pol. AUG  | GGG TTG AAA AAC ATA GCG GAC | P = S |
| 4  | 2729 | 172755–172775 | IE1 AUG       | GAG GAC TCC ATC GTG TCA AG  | P = S |
| 5  | 2855 | 78445–78465   | DNA pol. coding | GTG GGC CAT GAT GGT GGA AGG | P = S |
| 6  | 2856 | 77903–77923   | DNA pol. coding | GTC CCG TAG ATG ACC CGC GCC | P = S |
| 7  | 2869 | 78688–78708   | DNA pol. coding | CGG CGC AGA TTG CAA GGG CGG | P = S |
| 8  | 2870 | 78655–78675   | DNA pol. coding | GCC GGA GCC GGG TGA AAC GCC | P = S |
| 9  | 2871 | 77305–77325   | DNA pol. coding | CGC CGT CCG GAC ACC GGG CGC | P = S |
| 10 | 2876 | 77250–77270   | DNA pol. coding | ACC GGG AAA CCA CGC CGG CGG | P = S |
| 11 | 2877 | 77155–77175   | DNA pol. coding | CCG CGC CCT CTT CTT TGC CGG | P = S |
| 12 | 2882 | 173601–173621 | IE1 int/exon 1 | GGT ACT TAC GTC ACT CTT GGC | P = S |
| 13 | 2883 | 172775–172795 | IE1 int/exon 2 | GAC GGT GAC TGC AGA AAA GAC | P = S |
| 14 | 2884 | 172686–172706 | IE1 int/exon 3 | GAC ACG TAC CGT GGC ACC TTG | P = S |
| 15 | 2890 | 172572–172591 | IE1 int/exon 4 | GTC TCG GGC CTA AAC ACA TG  | P = S |
| 16 | 2891 | 172387–172406 | IE1 int/exon 5 | CAG ACT TAC CGA CTT CTG CC  | P = S |
| 17 | 2908 | 172218–172237 | IE1 int/exon 6 | CTG TTT GAC TGT AGA GGA GG  | P = S |
| 18 | 2918 | 170373–170393 | IE2 AUG       | GGG TCC TTC ATC TGG GAG AGC | P = S |
| 19 | 2919 | 170004–170024 | IE2 int/exon 1 | CGG CTC ACC TCG TCA ATC TTG | P = S |
| 20 | 2920 | 169535–169555 | IE2 int/exon 2 | GCG CAC CAT GAC CTG TTT GGG | P = S |
| 21 | 2921 | 170652–170672 | IE2 nuc sig 1 | GTT TTG CGC GGT TTC TTA CGC | P = S |
| 22 | 2922 | 170120–170140 | IE2 nuc sig 2 | GCG TTT GCT CTT CTT CTT GCG | P = S |
| 23 | 3245 | 173713–173733 | IE1/IE2 5'cap | CGT CTC CAG GCG ATC TGA CGC | P = S |
| 24 | 3246 | 173710–173730 | IE1/IE2 5'cap | TGG CGT CTC CAG GCG ATC TGA | P = S |
|    | 3258 | "             | "             | "                           | 2'-O—Me |
|    | 3300 | "             | "             | "                           | P = S/2'-O—Me |
| 25 | 3224 |               | Random        | TCT GAG TAG CAG AGG AGC TC  | P = S/2'-O—Me |

TABLE 2-continued

Oligonucleotides Tested for Activity Against CMV

| SEQ ID NO | ISIS # | NUCLEOTIDE #s | TARGET | SEQUENCE | TYPE |
|---|---|---|---|---|---|
| 26 | 3221 | | Random | CTC CAC GCG AAT TTT AAC ACA | P = S |
|    | 3266 | | "      | "                             | 2'-O—Me |
| 27 | 1238 | | Random | ACT CGG GCT GCC ACT TGA CAG | P = S |

Of the oligonucleotides tested, eight were complementary to mRNA encoding the HCMV DNA polymerase, and the remainder were complementary to RNA transcribed from the major immediate early promoter of HCMV. Since the two major protein products from this genomic region (IE1 and IE2) are synthesized from messenger RNA, which is transcribed from a common promoter, eight of these compounds are complementary to both the IE1 and IE2 mRNA. Three compound are complementary only to the IE1 and IE2 mRNA. Three compounds are complementary only to the IE1 mRNA, and the remaining five are specific for IE2 mRNA.

Figure 2:
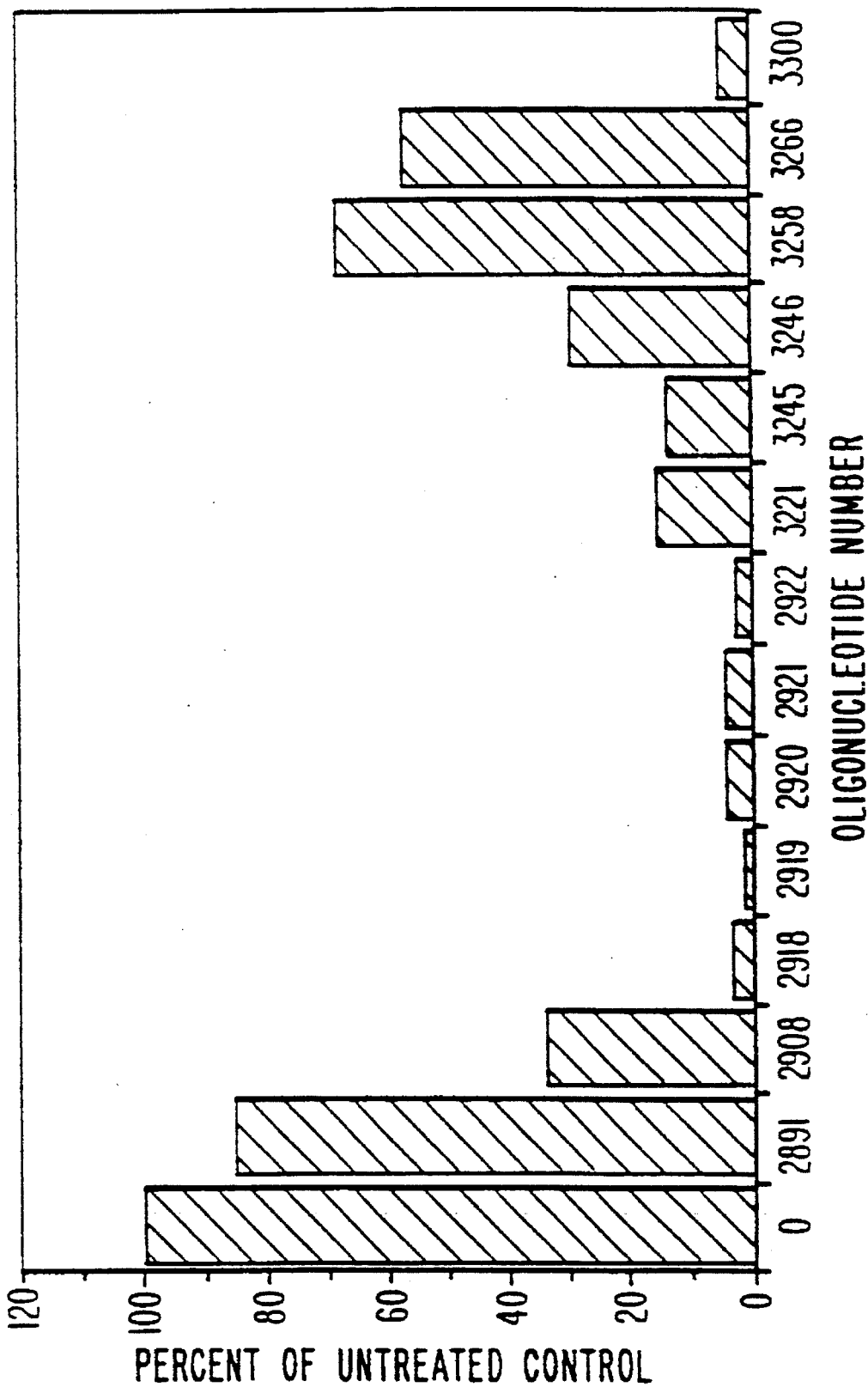
FIG. 2 is a bar graph showing the antiviral activity of oligonucleotides 2891 through 3300 against cytomegalovirus.

At a screening concentration of 5 μM all but one compound showed some reduction of viral replication compared to untreated cells (FIGS. 1 and 2). Some compounds exhibited a markedly greater inhibition of virus replication than control oligonucleotides, and these were chosen for further characterization.

Figure 3:
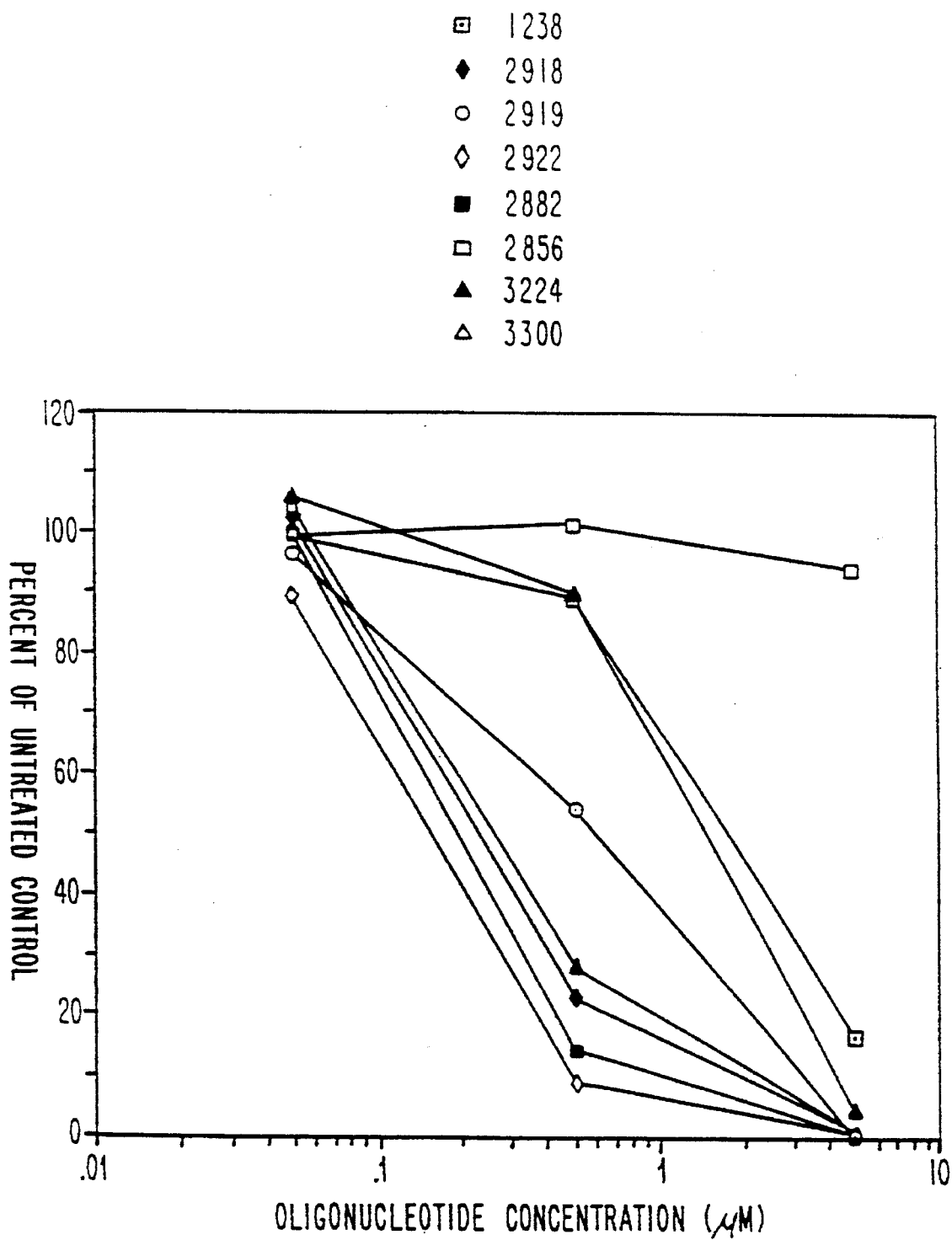
FIG. 3 is a line graph showing antiviral effects of eight oligonucleotides at doses from 0.01 to 10 μM.
Figure 4:
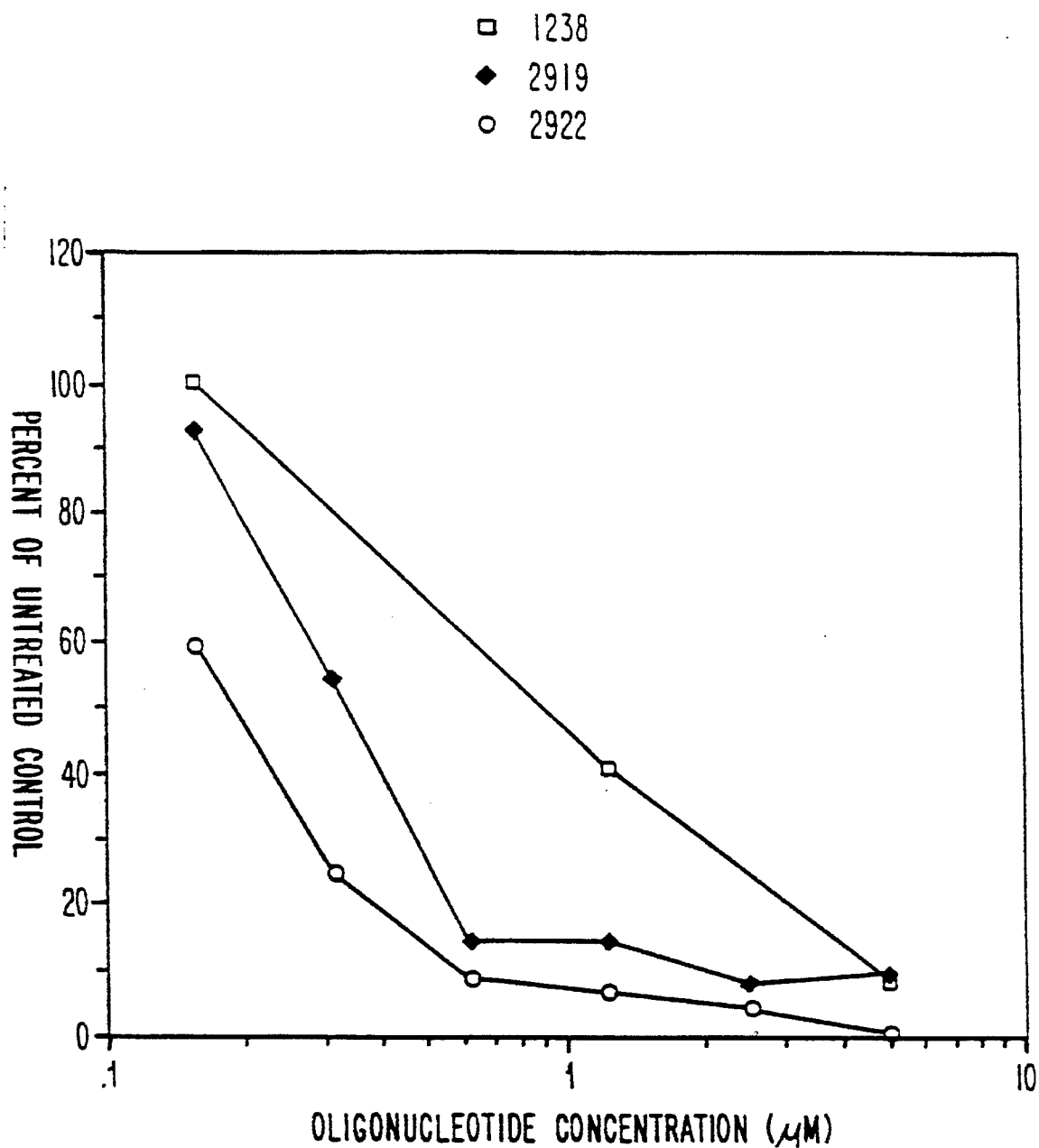
FIG. 4 is a line graph showing antiviral effects of three oligonucleotides at doses from 0.1 to 10 μM.

Dose-response experiments differentiated between non-specific effects and sequence-specific inhibition of HCMV replication by antisense oligonucleotides. Compounds ISIS 2922 (SEQ ID NO: 22), ISIS 2882 (SEQ ID NO: 12), ISIS 2918 (SEQ ID NO: 18), ISIS 2919 (SEQ ID NO: 19) and ISIS 3300 (SEQ ID NO: 24, P=S/2'—O—Me) all showed inhibition of HCMV replication at lower doses than randomized oligonucleotides with no complementarity to HCMV (FIG. 3). Compounds ISIS 2918 (SEQ ID NO: 18), ISIS 2919 (SEQ ID NO: 19), and ISIS 2922 (SEQ ID NO: 22) are complementary to IE2 RNA sequences. ISIS 2882 (SEQ ID NO: 12) and ISIS 3300 (SEQ ID NO: 24, P=S and 2'—O—Me) are complementary to the 5' cap region of IE1 and IE2 transcripts. Except where indicated in Table 2, oligonucleotides used are phosphorothioates; ISIS 3300 contains 2'-O-methyl-modified nucleosides with phosphorothioate linkages. This double modification was shown to convey much stronger antiviral activity upon the oligonucleotide than either the phosphorothioate (ISIS 3246, moderate activity) or the 2'-O-methyl modification (ISIS 3258, slight activity) alone. The activity of ISIS 2919 and ISIS 2922 relative to a randomized control oligonucleotide was confirmed in an independent dose-response experiment (FIG. 4).

What is claimed is:

1. An oligonucleotide or oligonucleotide analog having 15 to 50 bases fully complementary to a target DNA or corresponding RNA or pre-messenger RNA sequence wherein said oligonucleotide is selected from group consisting of SEQ ID NO:s 3–21, 23 and 24 and said oligonucleotide analog is selected from the group consisting of: modified SEQ ID NO:s 3–21, 23 and 24 as set forth in Table 2.

2. A method for inhibiting replication of cytomegalovirus comprising contacting cells in vitro infected with CMV with an oligonucleotide analog fully complementary to a target DNA or corresponding RNA or pre-messenger RNA sequence wherein said oligonucleotide analog is selected from the group consisting of: modified SEQ ID NO:s 3–21, 23 and 24 as set forth in Table 2.

* * * * *

UNITED STATES PATENT AND TRADEMARK OFFICE
CERTIFICATE OF CORRECTION

PATENT NO. : 5,591,720

DATED : January 7, 1997

INVENTOR(S) : Anderson et al.

It is certified that error appears in the above-indentified patent and that said Letters Patent is hereby corrected as shown below:

Column 3, lines 14/15, "Oligonucleotides: Antisense Inhibitors of Gene Expression" should be in italics.

Column 10, line 34, please delete "gens" and insert therefor --gene--.

Column 10, line 45, please delete immuneprecipitation" and insert therefor --immunoprecipitation--.

Column 10, line 46, please delete immuneprecipitate" and insert therefor --immunoprecipitate--.

Column 11, line 19, please delete "2'O-methyl" and insert therefor --2'-O-methyl--.

Column 27, line 5, after "from" and before "group", please insert --the--.

Signed and Sealed this

Twenty-fourth Day of June, 1997

Attest:

BRUCE LEHMAN

*Attesting Officer*          *Commissioner of Patents and Trademarks*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

GTGTCAAGTG GCACCATACG                                                    2 0

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

TGGAAAGTGT ACACAGGCGA A                                                                                      21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:3:

GGGTTGAAAA ACATAGCGGA C                                                                                      21

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

GAGGACTCCA TCGTGTCAAG                                                                                         20

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:5:

GTGGGCCATG ATGATGGAAG G                                                                                       21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:6:

GTCCCGTAGA TGACCCGCGC C                                                                                       21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:7:

CGGCGCAGAT TGCAAGGGCG G        21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:8:

GCCGGAGCCG GGTGAAACGC C        21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:9:

CGCCGTCCGG ACACCGGGCG C        21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:10:

ACCGGGAAAC CACGCCGGCG G        21

( 2 ) INFORMATION FOR SEQ ID NO:11:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:11:

CCGCGCCCTC TTCTTTGCCG G        21

( 2 ) INFORMATION FOR SEQ ID NO:12:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:12:

GGTACTTACG TCACTCTTGG C        21

( 2 ) INFORMATION FOR SEQ ID NO:13:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:13:

GACGGTGACT GCAGAAAAGA C        21

( 2 ) INFORMATION FOR SEQ ID NO:14:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:14:

GACACGTACC GTGGCACCTT G        21

( 2 ) INFORMATION FOR SEQ ID NO:15:

( i ) SEQUENCE CHARACTERISTICS:
    ( A ) LENGTH: 20 base pairs
    ( B ) TYPE: nucleic acid
    ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:15:

GTCTCGGGCC TAAACACATG                                                                    20

( 2 ) INFORMATION FOR SEQ ID NO:16:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:16:

CAGACTTACC GACTTCTGCC                                                                    20

( 2 ) INFORMATION FOR SEQ ID NO:17:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:17:

CTGTTTGACT GTAGAGGAGG                                                                    20

( 2 ) INFORMATION FOR SEQ ID NO:18:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:18:

GGGTCCTTCA TCTGGGAGAG C                                                                  21

( 2 ) INFORMATION FOR SEQ ID NO:19:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: DNA (genomic)

(i i i) HYPOTHETICAL: NO (i v) ANTI-SENSE: YES (x i) SEQUENCE DESCRIPTION: SEQ ID NO:19:

CGGCTCACCT CGTCAATCTT G 21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:20:

GCGCACCATG ACCTGTTTGG G 21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:21:

GTTTTGCGCG GTTTCTTACG C 21

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:22:

GCGTTTGCTC TTCTTCTTGC G 21

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES ( x i ) SEQUENCE DESCRIPTION: SEQ ID NO:23:

CGTCTCCAGG CGATCTGACG C　　　　　　　　　　　　　　　　　　　　　　　21

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:24:

TGGCGTCTCC AGGCGATCTG A　　　　　　　　　　　　　　　　　　　　　　　21

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:25:

TCTGAGTAGC AGAGGAGCTC　　　　　　　　　　　　　　　　　　　　　　　　20

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:26:

CTCCACGCGA ATTTTAACAC A　　　　　　　　　　　　　　　　　　　　　　　21

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:27:

ACTCGGGCTG CCACTTGACA G　　　　　　　　　　　　　　　　　　　　　　　21